US00PP20893P3

(12) United States Plant Patent
Lowe et al.

(10) Patent No.: US PP20,893 P3
(45) Date of Patent: Mar. 30, 2010

(54) KIWI PLANT NAMED 'HORT22D'

(50) Latin Name: *Actinidia chinensis*
Varietal Denomination: Hort22D

(75) Inventors: Russell G. Lowe, Te Puke (NZ); Canhong Cheng, Rotorua (NZ)

(73) Assignee: Zespri Group Limited, Mount Maunganui South (NZ)

( * ) Notice: Subject to any disclaimer, the term of this patent is extended or adjusted under 35 U.S.C. 154(b) by 0 days.

(21) Appl. No.: 12/148,333

(22) Filed: Apr. 18, 2008

(65) Prior Publication Data

US 2008/0289070 P1 Nov. 20, 2008

Related U.S. Application Data

(60) Provisional application No. 60/925,165, filed on Apr. 18, 2007.

(51) Int. Cl.
*A01H 5/00* (2006.01)

(52) U.S. Cl. ..... Plt./156

(58) Field of Classification Search ..... Plt./156
See application file for complete search history.

(56) References Cited

U.S. PATENT DOCUMENTS

PP11,066 P 9/1999 Lowe et al.

*Primary Examiner*—Susan B McCormick Ewoldt
(74) *Attorney, Agent, or Firm*—Knobbe, Martens, Olson & Bear LLP

(57) ABSTRACT

A new and distinct kiwifruit variety is disclosed. The variety results from selection among a population of seedlings derived from crossing the kiwifiuit selections known as CK5 1_06 (not patented) and CK51_11 (not patented). The fruit of the plant of this new kiwifruit variety is characterized by its internal red color and early harvest maturity. The new kiwifruit variety has been named 'Hort22D'.

5 Drawing Sheets

Latin name of the genus species of the plant claimed: *Actinidia chinensis.*

Variety denomination: 'HORT22D'.

CROSS-REFERENCE TO RELATED APPLICATIONS

This application claims the benefit of U.S. Provisional Application No. 60/925,165, filed on April 18, 2007, the entire contents of which are hereby incorporated by reference and should be considered a part of this specification.

BACKGROUND AND SUMMARY OF THE INVENTION

The invention relates to the discovery and asexual propagation of a new and distinct variety of kiwifruit, *Actinidia chinensis* cv. 'Hort22D', as herein described and illustrated. The new kiwifruit variety 'Hort22D' was selected from a population of seedlings derived from crossing two unpatented kiwifruit selections CK51-06 (unpatented), the female parent, and CK51-11 (unpatented), the male parent, in the course of a planned kiwifruit variety breeding program. The cross was made in October 1996 at Te Puke, Bay of Plenty, New Zealand. The new variety was selected as 52.13.22D (breeder reference) and has been named 'Hort22D'.

The new kiwifruit variety 'Hort22D' may be distinguished from presently available *Actinida chinensis* cultivars by the following distinguishing characteristics. The fruit of the new kiwifruit variety 'Hort22D' matures earlier than the fruit of 'Hort16A' (U.S. Plant Pat. No. 11,066). The new kiwifruit variety 'Hort22D' produces much sweeter fruit having a strong expression of red color in the flesh.

The new kiwifruit variety 'Hort22D' may be distinguished from other presently available kiwifruit varieties featuring red-flesh fruit such as, for example, 'Hongyang' (not patented) and 'Red Princess' (not patented), by the following distinguishing characteristics. The fruit shape of the new variety 'Hort22D' is oblong compared with that of 'Hongyang', which is obovoid. The fruit shape at the stylar ends of the new variety 'Hort22D' is slightly protruding compared with that of 'Hongyang', which is hollow. The fruit of 'Hort22D' also matures earlier and is larger in size than those of 'Hongyang'. Furthermore, the expression of red color in flesh of the new variety 'Hort22D' is very strong compared with that of 'Red Princess', which is weak. In addition, 'Hort22D' is diploid compared with 'Red Princess', which is tetraploid. The new kiwifruit variety 'Hort22D' may be distinguished from the female (fruiting) parent by the following characteristics: fruit of CK51-06 is more elongated and the red pigment in the flesh is within the locule and has a restricted spread of approximately one third of the locule length, whereas the expression in fruit of the new variety 'Hort22D', is developed in approximately 80% of the locule length. Further, the cavity expressed in some fruit of the new variety 'Hort22D' does not occur in fruit of CK51-06, and the flowering period for the female parent commences approximately one week prior to that for the new variety, although is similar in duration.

Asexual propagation of the new kiwifruit variety 'Hort22D' by grafting shows that the unique combination of characteristics of the variety come true to form and are established and transmitted through succeeding propagation. In order to obtain true-to-type clones of the initial plant, asexually propagated plants were obtained by grafting dormant buds from the original seedling onto rootstocks. The new variety 'Hort22D' was first asexually propagated at Te Puke, Bay of Plenty, New Zealand.

BRIEF DESCRIPTION OF THE FIGURES

The accompanying figures illustrate in full color typical specimens of the fruit, flowers, and leaves of the new variety cv. 'Hort22D'. The colors as depicted are as nearly true as is reasonably possible in a color representation of this type.

DETAILED BOTANICAL DESCRIPTION OF THE INVENTION

The following is a detailed description of the new variety. The specimens described were grown at Te Puke, Bay of Plenty, New Zealand. The observations were made in the 2003 to 2007 seasons on vines grafted onto existing clonal 'Brono' rootstock, and managed under standard orchard practice. Random measurements of each characteristic were obtained from samples of 10 plants unless otherwise stated.

Horticultural terminology is used in accordance with UPOV guidelines for kiwi. All dimensions are in millimeters, and all weights are in grams (unless otherwise stated). Certain characteristics of this variety, such as growth and color, may change with changing environmental conditions (e.g., light, temperature, moisture), nutrient availability, rootstocks, or other factors. Color descriptions and other terminology are used in accordance with their ordinary dictionary descriptions, unless the context clearly indicates otherwise. Color names beginning with a capital letter designate values based upon The R.H.S. Colour Chart published by the Royal Horticultural Society, London, England.

PLANT AND FOLIAGE

The plant is a female plant that is diploid and expresses a twining habit of low to medium vigor.

Figure 6:
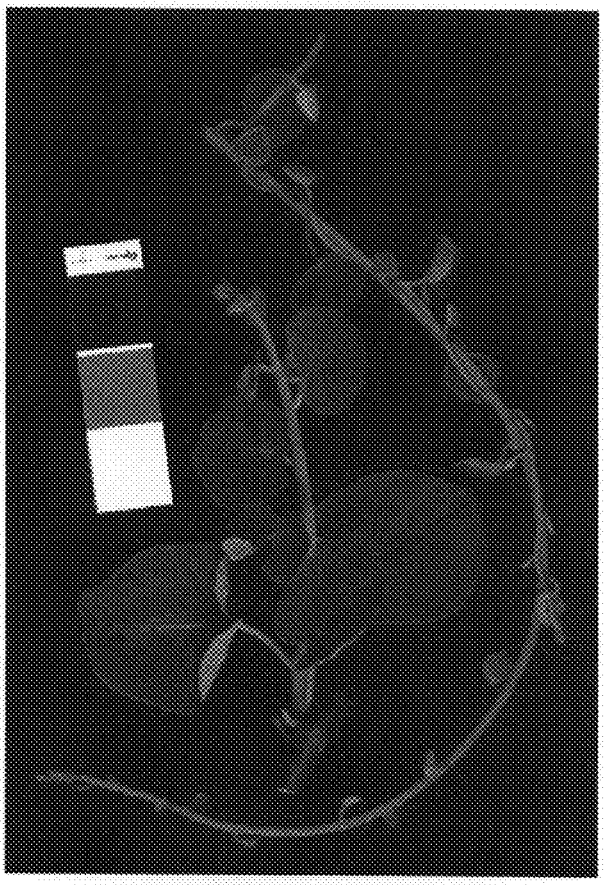
FIG. 6 is a photograph of immature leaves of the new kiwifruit variety 'Hort22D'.

Tomentose hairs are present on the young shoot at medium density. Anthocyanin (Red) coloration of the growing tip is present (R.H.S. 181B) (FIG. 6).

The stem of the plant is smooth bark and colored Dark-brown (R.H.S. 200B) on the upper side. Hairs are absent from the plant stem, but there are a few White lenticels (R.H.S. 159C). The size of the bud support is small and the leaf scar is shallow. Stems are of medium thickness, averaging 12.4 mm in diameter and buds on these stems are 7.6 mm wide on average. A bud cover is present on these stems. Few lenticels are present; incidence averages approximately 7 lenticels per $cm^2$ of stem section, with each lenticel averaging approximately 1 mm to 2 mm in length and 0.5 mm to 1.0mm wide.

Figure 5:
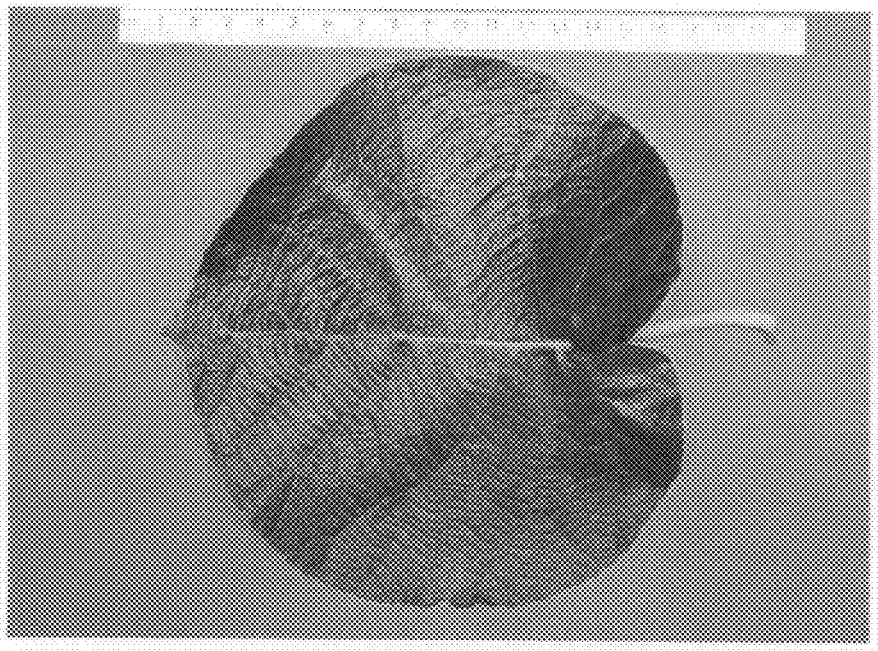
FIG. 5 is a photograph of a mature leaf of the new kiwifruit variety 'Hort22D'.

Leaves are arranged alternately on the plant. The mature leaf is broad ovate in shape with a rounded leaf tip (FIG. 5) and typically averages approximately 132 mm in length and approximately 140 mm in width. The leaf bases are slightly overlapping. The color of the leaf blade is Medium Dark-green (R.H.S. 139A) on the upper surface and Yellow-green (R.H.S. 137C) on the lower surface. The leaf margin is crenulated and venation pattern is reticulate. Leaves have a few hairs, but only on the mid rib of the leaf surface. Leaf petioles average approximately 124 mm and have medium anthocyanin coloration on the upper side of the petiole in some cases (R.H.S. 58C), but petioles are predominantly a Grey-yellow color (R.H.S.160A). Petioles have a relatively dense covering of hairs.

INFLORESCENCE

The number of flowers in each inflorescence is typically between one to four flowers, with each inflorescence comprising a single king flower and one or two side flowers (0.4 per inflorescence on average). Each one-year-old shoot, typically develops three or four inflorescences, with an average of 3.6.

Pedicels average approximately 38.1 mm in length and are densely covered in short hair.

Figure 4:
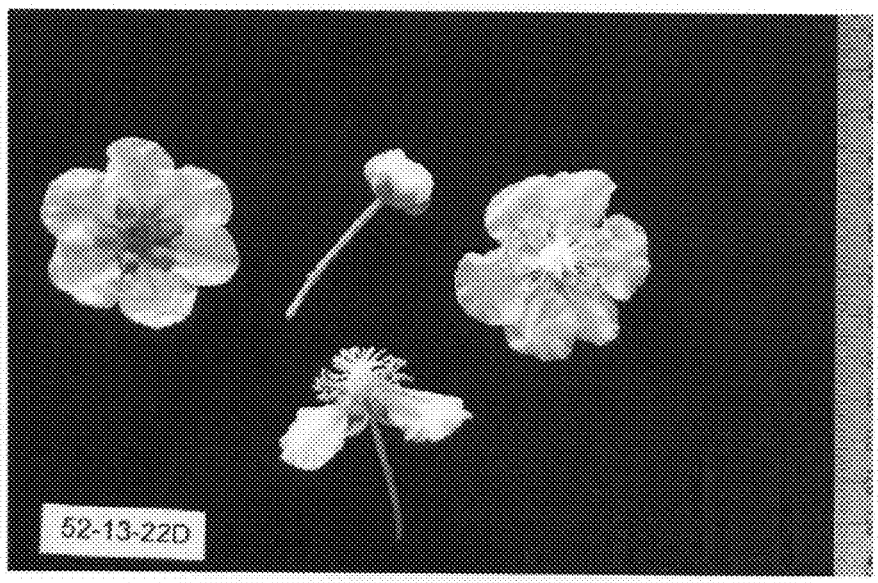
FIG. 4 is a photograph of the flowers of the new kiwifruit variety 'Hort22D'.

Flower buds average approximately 15 mm in diameter and are near Light-green (R.H.S. 144B) in color. There are between six and eight petals on each flower, with an average of 6.5. The flowers are rotate in form, the petals are arranged overlapping and both surfaces are White in color (R.H.S. 158C) when fully open, but with a Light-green base (R.H.S. 144B) (FIG. 4). The petals are revolute; petals are weakly curved at the apex. Flowers also contain between five and six sepals that are Green in color (R.H.S. 145B). The diameter of the king flower ranges from 43 mm to 52 mm, averaging approximately 49 mm. Each flower produces between 31 and 48 styles (39 on average) with a semi-erect attitude, that are six mm long on average and White in color (R.H.S. 155D). Between 50 to 68 stamens (55 on average) are also present on each flower, with filaments that are seven mm long on average and vary from Green in color at their base (R.H.S. 144B) to White in color near the anthers (R.H.S. 155D). Anthers are three mm long on average and are Yellow-orange in color (R.H.S. 18A). No discernable fragrance has been observed.

Ovaries of the king flower are covered in fine hairs that are While in color (R.H.S. 155D). Anthocyanin (Red) coloration of the ovary in cross section is present in the outer pericarp (R.H.S. 50B). Ovaries of the king flower have a mean length of six mm and are oblong in shape.

FRUIT

Figure 1:
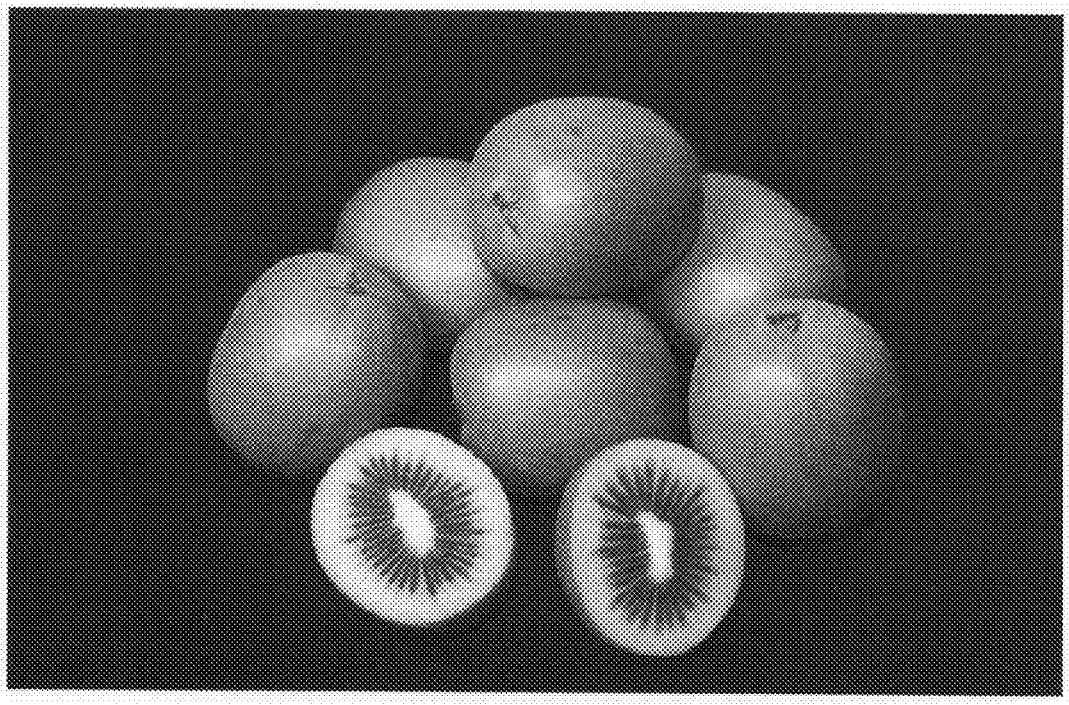
FIG. 1 is a photograph of the fruit of the new kiwifruit variety 'Hort22D'.
Figure 2:
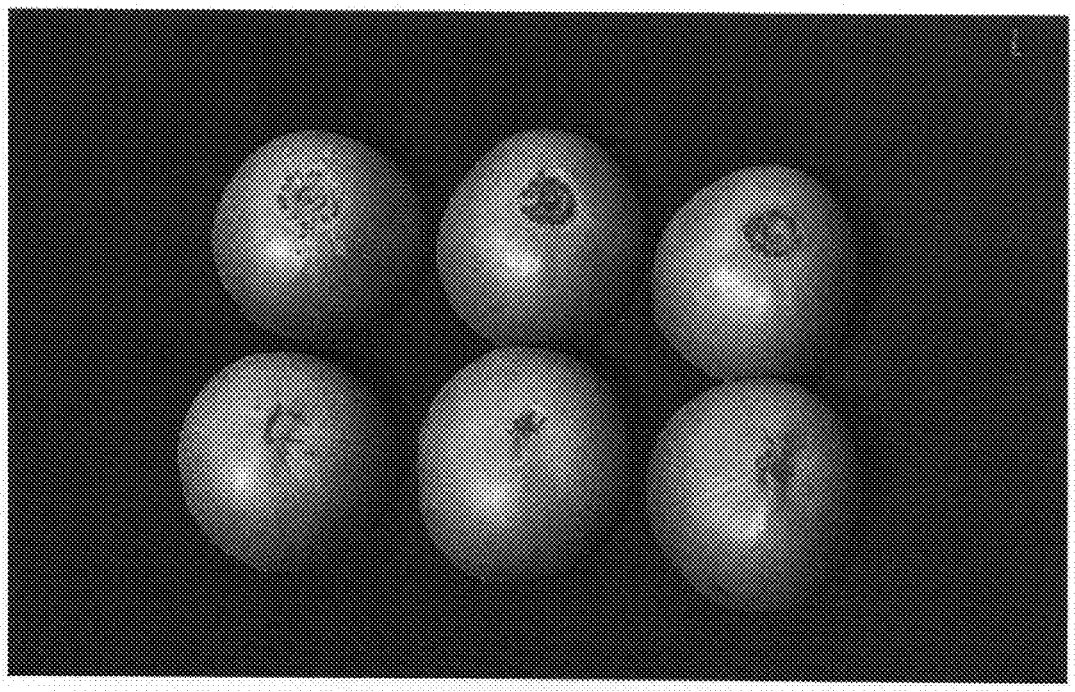
FIG. 2 is a photograph of the stem and stylar end views of the fruit of the variety 'Hort22D'.

The fruit overall are small to medium in size, averaging approximately 69.2 g in weight. The dimensions of the fruit average 51.6 mm in length and 49.0 mm maximum width, with maximum core diameter averaging 18.4 mm. The general fruit shape in longitudinal section is oblong, with the general shape of the stylar end being slightly blunt protruding (FIGS. 1 and 2). In cross section, the fruit shape at the median part of the fruit varies between circular and elliptic, with most fruit being at least partially elliptic in shape.

Fruit stalks are short, averaging 38 mm long and 2.8 mm in diameter and are Brown in color (R.H.S. 199B).

Figure 3:
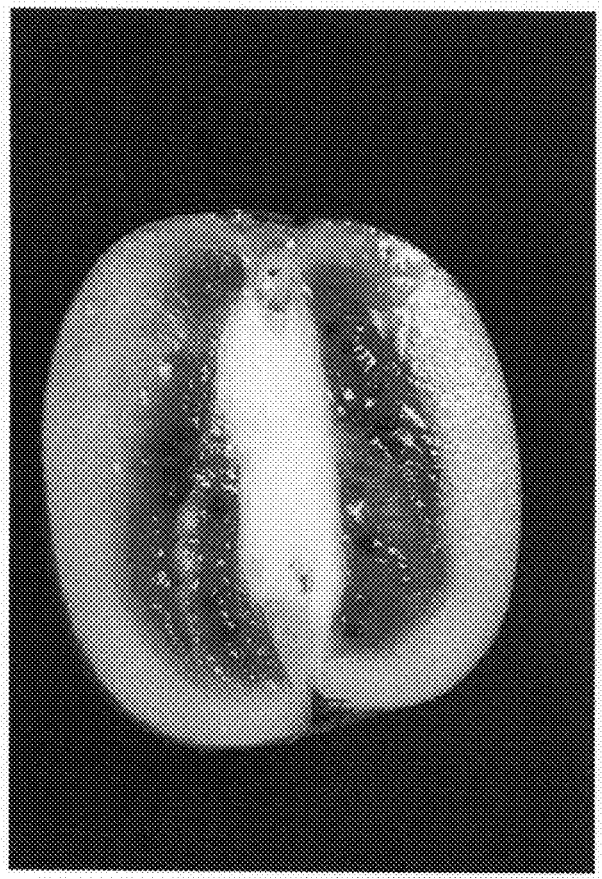
FIG. 3 is a photograph of the fruit of the new kiwifruit variety 'Hort22D' in longitudinal-section revealing the fruit's red pigmentation at maturity for consumption.
Figure 7:
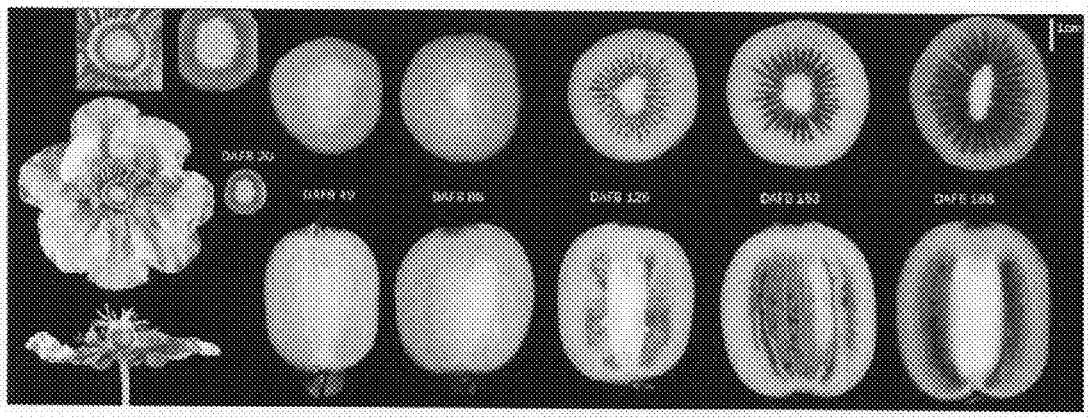
FIG. 7 is a photograph of the ovary and fruit in cross section and longitudinal section at different stages of development as determined by days after full bloom (DAFB) of the new kiwifruit variety 'Hort22D'.
Figure 8:
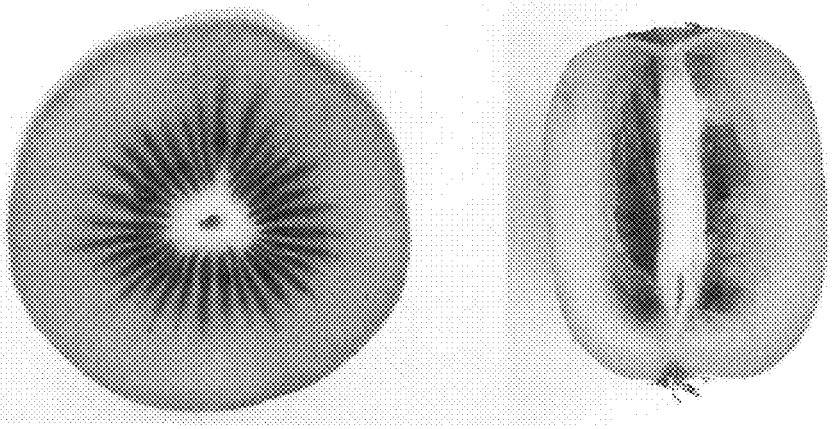
FIG. 8 is a photograph of the core cavity present in the fruit of the new kiwifruit variety 'Hort22D'.

Downy, medium density fruit hairs are present on the young fruitlets, but hairs are very short and the fruit appear smooth and almost hairless when mature. The skin of the fruit remains Green in color (R.H.S. 146B) when the fruit have been completely protected from direct sun exposure, but the skin changes to Brown in color (R.H.S. 165B) on exposed fruit. The skins are covered with numerous lenticels that are Light Orange-white in color (R.H.S. 159C), but are relatively inconspicuous. The outer pericarp loses the anthocyanin pigmentation within 35 days of flowering and becomes a Light-green color (R.H.S. 149B). The outer pericarp then gradually changes to a Yellow color (R.H.S. 11B) over a six to eight week period, as the fruit mature during March and early April in the Te Puke region of New Zealand. The inner pericarp is colored Red (R.H.S. 45B) at maturity for consumption (FIG. 3), with anthocyanin pigments evident in the inner pericarp from December in the Te Puke region of New Zealand (FIG. 7). The core of the mature fruit is White (R.H.S.158D) and irregularly elliptic in shape. In almost all (93%) of the fruit, a cavity can be observed near the base of the core (FIG. 8). The fruit contain between 32 and 41 locules (37 on average) and between 20 and 36 seeds (27 on average) can be counted on a transverse slice made through the middle of the fruit. Mature seeds are Dark-brown in color (R.H.S. 200A).

'Hort22D' plants can be grown on the same rootstocks as other standard varieties such as 'Hayward' and 'Hort16A'. Rootstocks currently being used in New Zealand include *A. deliciosa* seedlings, *A. chinenis* seedlings, and 'Kaimai' (not patented). Under commercial cultivation, plants are typically grown with two leaders expanding into a trained canopy comprising stems spaces at approximately 300 mm and with a typical length of 1 m to 2 m.

Fruit flavor is very sweet with flavor characteristics of both 'Hayward' and 'Hort16A' kiwifruit. The fruit start to ripen soon after they have been harvested in late March and early April in the Te Puke region of New Zealand and will reach eating ripeness within two weeks if they are not stored at low temperatures. Fruit that are harvested before they are ripe will continue to accumulate soluble solids as starch is converted to soluble sugars. The fruit average 16.8% soluble solids (measured as Brix) and contain 198 mg of vitamin C per 100 g of fresh weight at maturity for consumption.

CULTIVATION

'Hort22D' plants can be grown on the same rootstocks as other standard varieties such as Hayward and 'Hort16A'. Rootstocks currently being used in New Zealand include *A. deliciosa* seedlings, *A. chinenis* seedlings, and 'Kaimai' (not patented).

Figure 9:
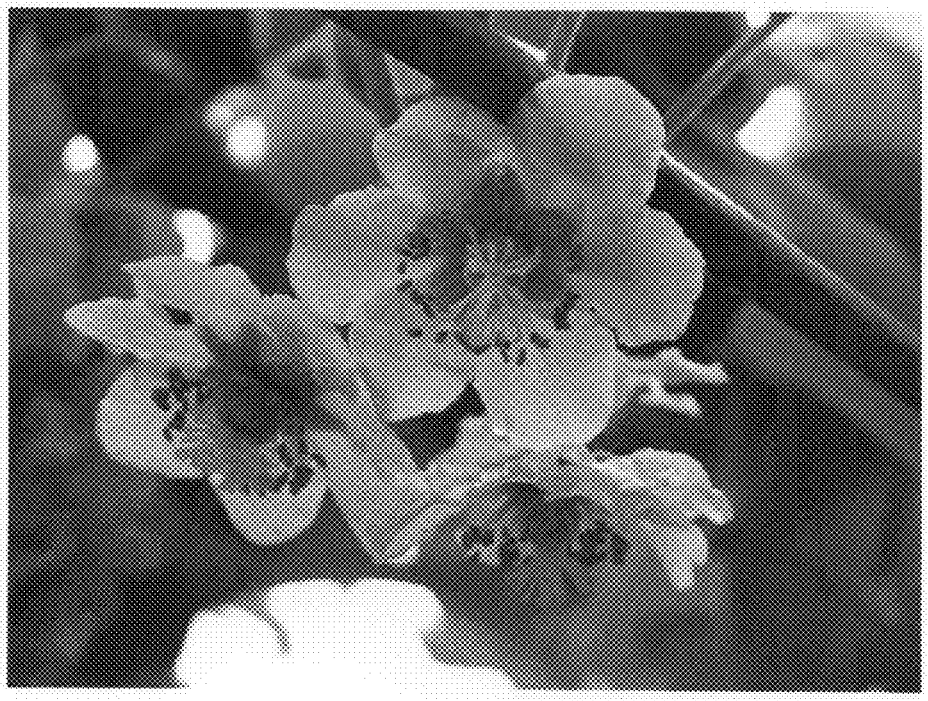
FIG. 9 is a photograph of the flowers of the new kiwifruit variety 'Hort22D' on a vine.

Vegetative bud break typically occurs in late August in the Te Puke region of New Zealand, with flowering commencing in mid October (FIG. 9). Between 43% and 68% of dormant buds burst in spring. Typically flowering commences about the 14th of October (approximately 5% of flower buds open) and finishes the 22nd of October (95% of flower buds open). Individual flowers are typically open 2-3 days before petal fall commences. The fruit attain maturity for harvest when they reach 10° Brix and 103° hue angle of the outer pericarp in approximately late March to early April in the Te Puke region of New Zealand. However, the harvest of fruit for long term cold storage is possible as early as the start of March in the Te Puke region of New Zealand. Leaves persist on the plants until early winter (June to July) in the Te Puke region of New Zealand. Geographical adaptation has not been fully determined although indications are that the variety is well-suited to production in the warm-temperate Bay of Plenty region of New Zealand. The plant cold hardiness according to the American zone classification has not been determined.

Figure 10:
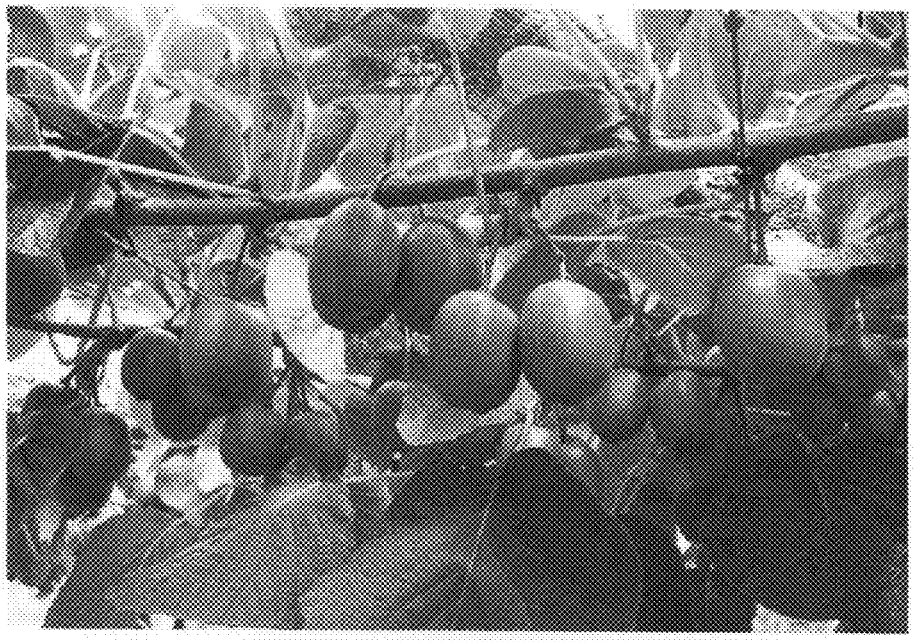
FIG. 10 is a photograph of the fruit of the new kiwifruit variety 'Hort22D' on a vine.

Plants produce very high flower numbers, with between 50 and 140 flowers per two-metre-long cane and crop loads of between 100 and 150 fruit per square meter of canopy produced in the absence of bud-break enhancing agents in the Te Puke region of New Zealand, prior to fruit thinning (FIG. 10). As a dioecious plant, a male pollinizer is required for effective pollination. Observations indicate the coincidence of timing between the female and male plant is more important for effective pollination than similarity in ploidy or species. Fruit yield is largely determined by the proportion of fruit that can be produced without surface markings and the proportion of fruit that have an acceptable fruit shape. To obtain a high proportion of marketable yield, 'Hort22D' fruit must be well protected from wind and direct sun for the first 90 days after flowering. Heavy thinning is required to reduce fruit numbers to a manageable crop load, to remove marked fruit and to remove fruit that do not meet grade standards for fruit shape. Natural fruit drop occurs prior to harvest, with 21% of fruit initially set dropping naturally from the plants during March in 2006 in the Te Puke region of New Zealand.

In post harvest storage, softening of harvested fruit can be delayed by placing fruit into cold storage in normal atmosphere or with a controlled atmosphere. In this case, fruit can be successfully stored for between 8 and 12 weeks while maintaining average flesh firmness greater than one kgf. Once removed from long term cold store and returned to ambient temperatures, the fruit continue to soften and must be consumed within approximately four days.

An additional surface marking that appears as dark spots on the skin sometimes develops between January and March and can be partially controlled with fungicide applications. Fruit are susceptible to *Sclerotinia* fungal infections soon after flowering. Results of controlled inoculations suggest that plants are substantially resistant to Latania Scale (*Hemiberlesia lataniae*) insects.

We claim:

1. A new and distinct kiwi plant substantially as herein described and illustrated, characterized by fruit with strong internal red color, oblong shape, and early harvest maturity.

* * * * *